United States Patent
Li et al.

(10) Patent No.: US 9,443,278 B2
(45) Date of Patent: Sep. 13, 2016

(54) METHOD AND APPARATUS FOR DATA CONVERSION IN AN UNEQUAL GAMMA ANGLE CT SYSTEM

(71) Applicant: GE MEDICAL SYSTEMS GLOBAL TECHNOLOGY COMPANY, LLC, Waukesha, WI (US)

(72) Inventors: Jun Li, Beijing (CN); Shuo Li, Beijing (CN); Juan Zhong, Beijing (CN); Jiaqin Dong, Beijing (CN); Abhishek Rawat, Bangalore (IN)

(73) Assignee: General Electric Company, Schenectady, NY (US)

( * ) Notice: Subject to any disclaimer, the term of this patent is extended or adjusted under 35 U.S.C. 154(b) by 194 days.

(21) Appl. No.: 14/165,957

(22) Filed: Jan. 28, 2014

(65) Prior Publication Data

US 2014/0211908 A1 Jul. 31, 2014

(30) Foreign Application Priority Data

Jan. 31, 2013 (CN) .......................... 2013 1 0037988

(51) Int. Cl.
*A61B 6/00* (2006.01)
*G06T 1/00* (2006.01)
*A61B 6/03* (2006.01)

(52) U.S. Cl.
CPC ................ *G06T 1/005* (2013.01); *A61B 6/032* (2013.01); *A61B 6/4233* (2013.01); *A61B 6/5205* (2013.01)

(58) Field of Classification Search
USPC ............................................ 378/1, 4, 11, 14
See application file for complete search history.

(56) References Cited

U.S. PATENT DOCUMENTS

| 4,570,224 A | 2/1986 | Shimoni et al. |
| 4,852,132 A | 7/1989 | Namikawa |
| 5,216,601 A | 6/1993 | Crawford et al. |
| 6,411,670 B1 | 6/2002 | Besson |
| 2006/0140335 A1* | 6/2006 | Heuscher .............. G06T 11/006 378/4 |

OTHER PUBLICATIONS

Defrise et al., Rebinning-Based Algorithms for Helical Cone-Beam CT, Physics in Medicine and Biology, vol. No. 46, Issue No. 11, pp. 2911-2937, Nov. 2001.
Kachelriess et al., "Advanced Single-Slice Rebinning in Cone-Beam Spiral CT", Medical Physics, vol. No. 27, Issue No. 4, pp. 754-772, Apr. 2000.

* cited by examiner

*Primary Examiner* — Nicole Ippolito
*Assistant Examiner* — Hanway Chang
(74) *Attorney, Agent, or Firm* — GE Global Patent Operation (57) ABSTRACT

A method and apparatus for data conversion in an unequal γ angle CT system. The method for imaging in a CT system having a flat module detector array includes obtaining fan beam projection data of an object from a CT scan, obtaining a geometric structure parameter of the flat module detector array; rebinning data from the fan beam projection data to parallel beam projection data based on the geometric structure parameter to convert the fan beam projection data into the parallel beam projection data, and generating a CT image from the parallel beam projection data.

13 Claims, 4 Drawing Sheets

METHOD AND APPARATUS FOR DATA CONVERSION IN AN UNEQUAL GAMMA ANGLE CT SYSTEM

TECHNICAL FIELD

The embodiments of the invention relate to medical scanning and, more particularly, to a method and an apparatus for imaging in a CT system having a flat module detector array.

BACKGROUND

With the development of medical technologies, medical scanning is becoming increasingly popular as an important diagnostic and treatment tool in many medical applications. For example, computed tomography (CT) has been widely used in diagnostic tests and radiotherapy for patients. In a CT system, an x-ray source projects a fan-shaped beam which is collimated to be within an X-Y plane of a Cartesian coordinate system, generally referred to as the "imaging plane". The x-ray beam passes through the object being imaged, such as a patient. The beam, after being attenuated by the object, impinges upon an array of radiation detectors. Then, the intensity of the attenuated x-ray beam is detected by the detector array to thus construct an x-ray image (i.e., CT image).

In the widely used third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In CT scanning, since the x-ray source projects a fan-shaped beam, the fan beam data is acquired instead of parallel beam data. However, the theory of imaging reconstruction was initially developed for parallel beam data. Therefore, one important step in CT imaging reconstruction is to rebin data from the fan beam data into parallel beam data to thus convert the fan beam projection data into the parallel beam projection data. By the data conversion, a set of fan beam detector samples taken during a scan by the CT system is converted into a set of equivalent parallel detector samples. This eliminates the distance weight otherwise required in fan beam reconstruction. Without the conversion to parallel beam projection data, the distance weight may cause a "zebra" or banding artifact across Z direction in reconstructing three dimensional data. Thus, data conversion from fan beam data to parallel beam data in the imaging reconstruction allows for a more direct and accurate implementation of reconstruction algorithms.

In third generation CT systems, all detector cells are uniformly distributed along the same arc whose center is the x-ray source. Currently, conversion from fan beam data to parallel beam data only focuses on the third generation curved detector. For example, the U.S. Pat. No. 6,411,670 patent describes a method for generating an enhanced object CT image, comprising rebinning the fan beam projection data obtained by the curved detector array with equal $\gamma$ angle into parallel beam projection data. All contents of this patent will be incorporated into the present application by reference.

Other prior art related to fan-to-parallel data rebinning includes U.S. Pat. No. 4,570,224, U.S. Pat. No. 5,216,601, U.S. Pat. No. 4,852,132, and etc. In addition, the following publications also involve fan-to-parallel data rebinning for a curved detector array, i.e., "Rebinning-based algorithms for helical cone-beam CT, 2001 Phys. Med. Biol. 46" and "Advanced single-slice rebinning in cone-beam spiral CT, Med. Phys. 27, April 2000". These patents and papers also are incorporated into the present application by reference.

The prior art to some extent alleviated the problem of applying fan beam projection data to CT image reconstruction. However, the prior art is inapplicable to the large flat module detector array, which has cost advantages. Different from traditional rebinning algorithms based on equal gamma ($\gamma$) angle geometry, the large flat module detector array has unequal $\gamma$ angle geometry. Applying the traditional rebinning algorithms to the flat module detector array may lead to incorrect rebinning results, and further causes severe ring artifacts.

There still exist other defects regarding fan-to-parallel data conversion in the prior art. Thus, it is desired that a new technical solution can improve the prior art in one or more aspects. For example, the new technical solution is expected to eliminate ring artifacts in use of the flat module detector array.

SUMMARY OF THE DESCRIPTION

The present invention aims to solve one or more problems in the prior art, and particularly to avoid such problems as ring artifacts caused by the flat module detector array.

According to an aspect of this invention, a method for imaging in a CT system having a flat module detector array is provided, the method comprising: obtaining fan beam projection data of an object from a CT scan; obtaining a geometric structure parameter of the flat module detector array; rebinning data from fan beam data to parallel beam data based on the geometric structure parameter to convert the fan beam projection data into the parallel beam projection data; and generating a CT image from the parallel beam projection data.

According to the method of one embodiment of this invention, rebinning data comprises re-sampling the data from the fan beam data to parallel beam data based on the geometric structure parameter to obtain a corresponding relation between the parallel beam projection data and the fan beam projection data.

According to the method of one embodiment of this invention, re-sampling data further utilizes the setting parameters of the CT scan.

According to the method of one embodiment of this invention, interpolation is applied to the fan beam projection data based on the corresponding relation between the parallel beam projection data and the fan beam projection data.

According to the method of one embodiment of this invention, rebinning data further comprises equally spacing the parallel beam projection data to generate equispaced parallel beam projection data, wherein a corresponding relation between the equispaced parallel beam projection data and the parallel beam projection data prior to spacing can be obtained by equally spacing the parallel beam projection data.

According to the method of one embodiment of this invention, equally spacing the parallel beam projection data comprises equally spacing the parallel beam projection data with a pre-determined distance.

According to the method of one embodiment of this invention, equally spacing the parallel beam projection data comprises applying interpolation to the parallel beam projection data based on the corresponding relation between the equispaced parallel beam projection data and the parallel beam projection data prior to spacing.

According to the method of one embodiment of this invention, the interpolation applied to the fan beam projection data is a 6th order Lagrange interpolation; and/or the interpolation applied to the parallel beam projection data is a 4th order Lagrange interpolation.

According to the method of one embodiment of this invention, obtaining fan beam projection data of the object from the CT scan comprises: when a helical scan is performed, interpolating the fan beam projection data obtained by the helical scan to obtain axial scan data.

According to the method of one embodiment of this invention, the CT image is generated by utilizing the parallel beam projection data based on a filtered back projection reconstruction algorithm.

According to the method of one embodiment of this invention, the method is also applicable to a curved detector array.

According to another aspect of this invention, an apparatus is provided for imaging in a CT system having a flat module detector array and obtaining fan beam projection data of an object from a CT scan, the apparatus comprising: parameter acquisition means for acquiring a geometric structure parameter of the flat module detector array; and data rebinning means for rebinning data from fan beam data to parallel beam data based on the geometric structure parameter to convert the fan beam projection data into the parallel beam projection data; wherein the CT system generates a CT image utilizing the parallel beam projection data.

According to yet another aspect of this invention, a CT system is provided, wherein the CT system comprises the method and/or apparatus in accordance with one of embodiments of this invention.

Embodiments of the present invention can solve one or more problems in the prior art. For example, embodiments of the present invention can prevent ring artifacts caused by the flat module detector array, and/or flexibly perform fan-to-parallel data conversion for various detector arrays.

BRIEF DESCRIPTION OF THE DRAWINGS

The advantages, features, and characteristics of the present invention can be better understood from the description that follows in conjunction with the attached drawings of the embodiments.

DETAILED DESCRIPTION

The present invention will be described more thoroughly by referring to the drawings which demonstrate exemplary embodiments. However, the present invention can be carried out in other manners and should not be construed as being limited by the specific embodiments. On the contrary, the embodiments are provided to enable the disclosure of the invention to be complete and sufficient, such that the conception can be better conveyed to those skilled in the art. In the text, the same or similar number indicates the same device or unit.

Figure 1:
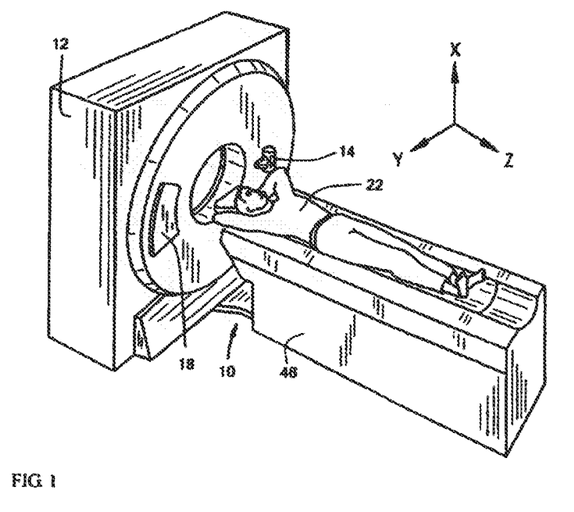
FIG. 1 shows a CT system according to one embodiment of the invention.

Referring to FIG. 1, a CT system 10 according to one embodiment of this invention is shown as including a gantry 12 representative of a third generation CT system. Gantry 12 has an x-ray source 14 that projects a fan beam of x-rays toward a detector array 18 on the opposite side of gantry 12. The detector array 18 is formed by a plurality of detector elements which together sense the projected x-rays that pass through a patient 22. Each detector element produces an electrical signal that represents the intensity of the impinging x-ray and hence the attenuation of the x-ray as it passes through patient 22 on the table 46. During a scan to acquire x-ray projection data, gantry 12 and the components mounted thereon rotate around a center of gantry 12 (i.e., the iso center). It should be understood that other than the third generation CT system mentioned herein, embodiments of the present invention is also applicable to any CT systems that require conversion from fan beam projection data to parallel beam projection data.

The detector array 18 as shown in FIG. 1 is a large flat module detector array comprising a plurality of flat modules and each flat module has a plurality of detector cells. For example, the flat module detector array comprises 5 large flat modules, and each module has 136 detector cells, which results in an unequal gamma ($\gamma$) angle geometry, that is, the differences between two $\gamma$ angles of any two adjacent detection channels are not equal. As the fan-to-parallel data rebinning is based on equal $\gamma$ angle geometry, the known data conversion or rebinning is not suitable for the flat module detector array.

Figure 2:
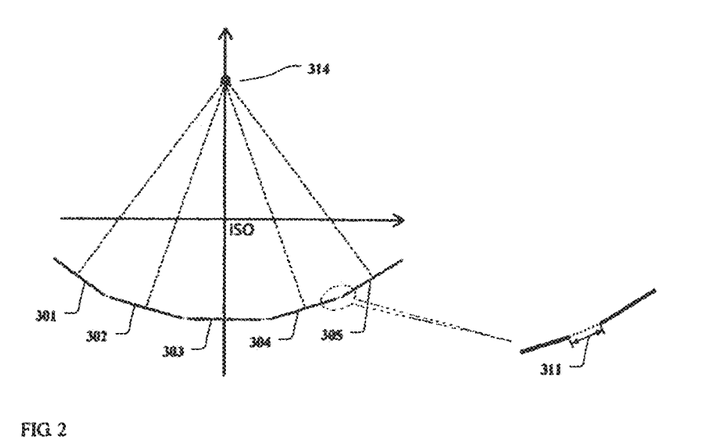
FIG. 2 shows a flat module detector array according to one embodiment of the invention.

FIG. 2 shows a flat module detector array according to one embodiment of the invention comprising flat modules 301-305. FIG. 2 also shows that there exists a gap 311 between modules 304 and 305. Meanwhile, FIG. 2 shows the x ray source 314.

Figure 3:
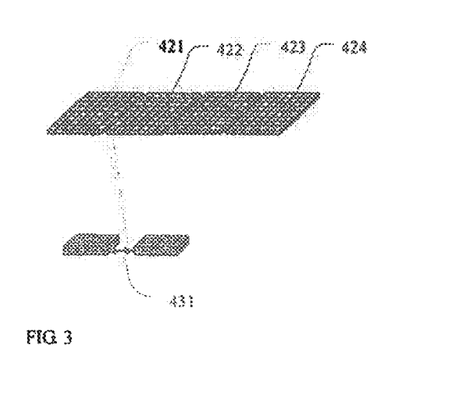
FIG. 3 shows the flat modules in a flat module detector array according to one embodiment of the invention.

FIG. 3 shows that one of modules 301-305 of the flat module detector array comprises a plurality of detector packs 421-424 and each pack further comprises a plurality of detector cells (for example, 34 detector cells). These detector cells constitute a plurality of detector rows (for example, 16 detector rows). FIG. 3 also shows that there exists a gap 431 between packs 421 and 422.

Though FIGS. 2 and 3 demonstrate the flat module detector array from different aspects, persons skilled in the art should understand that the specific flat module detector array shown in the drawings do not limit the invention. For example, the flat module detector array may also comprise more than or less than 5 modules and each module may comprises more than or less than 4 detector packs. Moreover, the numbers of detector cells, detector rows and detector channels may be changed as necessary. Furthermore, the gaps between modules, and the gaps between detector packs and/or other parameters may also be different from those shown in FIGS. 2 and 3.

Figure 4:
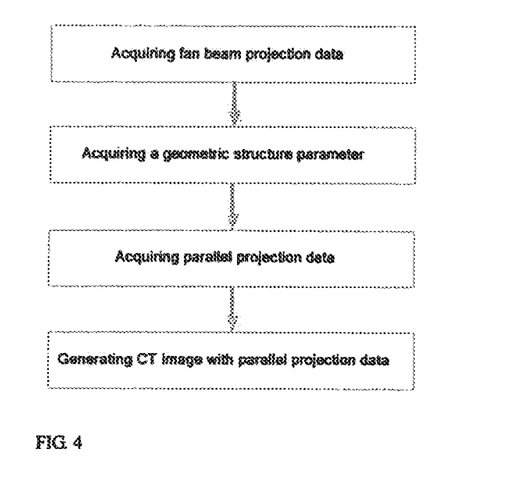
FIG. 4 shows a method for imaging in the CT system according to one embodiment of the invention.

FIG. 4 shows a method for imaging in the CT system having a flat module detector array according to one embodiment of the invention. In the imaging method, fan beam projection data of an object is obtained from a CT scan and a geometric structure parameter of the flat module detector array is also acquired. Then, the fan beam projection data is rebinned from fan beam data to parallel beam data based on the geometric structure parameter to convert the fan beam projection data into the parallel beam projection data. Next, a CT image is generated from the parallel beam projection data.

The geometric structure parameters of the flat module detector array may include, but not limited to: the number of flat modules, the number of detector packs in one module, the number of detector cells in one detector pack, the number of detector rows, the gap between two adjacent modules, and the gap between two adjacent packs in a same module. Moreover, the geometric structure parameters may also include the distance from x-ray source to iso-detector, the distance from x-ray source to iso-center, the detector cell size in x direction, and channel offset along x direction, etc. In the prior art, these parameters are well known. For example, channel offset along x direction refers to the offset of the line connecting x-ray source with iso-center (i.e., iso-ray) with respect to the middle channel (i.e., iso channel) of the detector array along x direction. As such, it is unnecessary to further elaborate these parameters here.

According to one embodiment of this invention, fan-to-parallel data rebinning further comprises re-sampling data from the fan beam data to parallel beam data based on the geometric structure parameter of the flat module detector array to obtain a relation between the parallel beam projection data and the fan beam projection data.

According to one embodiment of this invention, during the fan-to-parallel data re-sampling, fan beam projection data is re-sampled into parallel beam projection data, wherein each parallel view will contain data that was acquired from the same absolute angle. Each detector cell in the parallel view corresponds to a detector with an absolute angle in a fan view, which absolute angel is the same as the angle of the parallel view. In other words, the parallel beam projection data in the parallel view correspond to the fan beam projection data in the fan view having the angle of the parallel view.

To facilitate the description, the parameters for use hereinafter are listed. It is noticeable that some parameters are related to geometry parameters of the detector array, while the other parameters are related to CT scan settings but not directly to geometry parameters of the detector array. The specific parameters are as below:

v—the index, of the current fan view;
m—the index of current flat module in a detector array;
n—the index of current detector pack in current module;
k—the index of current cell in current detector pack;
$N_{mod}$—the number of flat modules;
$N_{pack}$—the number of detector pack in one module;
$N_{cells}$—the number of detector cells in one detector pack;
c—the index of the current detector channel, where $c = m*N_{cells}*N_{pack} + n*N_{cells} + k$;
r—the index of the current detector row;
$v_{total}$—the number of views available from the scan file;
$v_{rot}$—the number of views in a single rotation of the detector array around iso-center;

$c_{iso}$—the index of the detector channel corresponding to the iso-ray;
$d_{s2d}$—the distance from x-ray source to iso-detector cell (i.e., the iso-detector cell intersecting with iso-ray);
$d_{s2i}$—the distance from x-ray source to iso-center;
$d_{gap1}$—the gap between two adjacent modules;
$d_{gap2}$—the gap between two adjacent detector packs in a same module;
$d_{det}$—the size of the detector cell in x direction;
$c_{offset}$—offset of channels in x direction;
α—the angle between two modules in poloidal direction (i.e., the angle between central channels of two adjacent modules connecting with x-ray source);
β—the projection angle of current view; and
γ—the angle between current channel c and central channel (i.e., iso channel) relative to the x-ray source.

Figure 5:
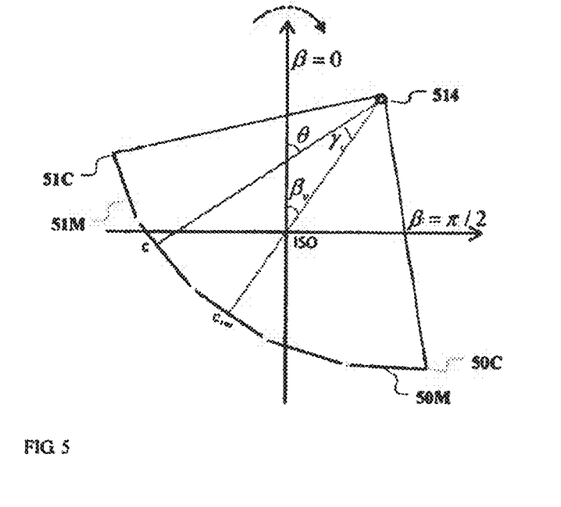
FIG. 5 shows a relationship between a fan view and a parallel view according to one embodiment of the invention.

FIG. 4 shows a relation between a fan view and a parallel view according to one embodiment of the invention, wherein the flat module detector array comprises a plurality of flat modules, including the 0th module 50M and the last module 51M. The 0th module 50M comprises the 0th channel 50C and the last module 51M comprises the last channel 51C. To be specific, the relationship between fan and parallel view for a given detector can be formulated as:

$$\theta = \beta_v + \gamma_c \quad (1),$$

where θ is the angle of the parallel view; $β_v$ is the angle of the current fan view indexed v, defined as the angle of the iso-ray with respect to the vertical axis in the clock-wise direction (such that β is always positive and increases as the view index v increases), and $γ_c$ is the angle at the source of the current channel c with reference to the iso-ray. So γ>0 is for channel indexes greater than iso channel and γ<0 is for channel indexes smaller than iso channel. So for a given channel c of current view, its corresponding angle $γ_c$ needs to be calculated firstly. In one embodiment, the geometric structure parameter of the flat module detector array needs to be considered in calculation of $γ_c$.

First, we need to get the module number m, which channel c belongs to, and the pack number n in this module, and also the cell number k in this pack. m, n and k can be obtained as follows:

$$m = (c - c \% (C_{cells}*N_{pack}))/(N_{cells}*N_{pack}),$$

$$k = (c - m*N_{cells}*N_{pack}) \% N_{cells},$$

$$n = (c - m*N_{cells}*N_{pack} - k)/N_{cells}, \quad (2)$$

and $γ_c$ can be described with m, n and k:

$$\gamma_c = \left(m - \frac{(N_{mod} - 1)}{2}\right)*a + \gamma_1 + \gamma_{offset} \quad (3),$$

where, $$a = 2a_1 + a_2,$$

$$a_1 = \mathrm{atan}((N_{cells}*N_{pack}*d_{det} + (N_{pack} - 1)*d_{gap2})/2/d_{s2d}),$$

$$a_2 = 2\mathrm{asin}\left(d_{gap1}/2 \bigg/ \left(\frac{d_{s2d}}{\cos a_1}\right)\right),$$

$$\gamma_1 = \mathrm{atan}\left(\left(\left(n - \frac{(N_{pack} - 1)}{2}\right)*d_{gap2} + \left(n*N_{cell} + k - \frac{(N_{pack}*N_{cell} - 1)}{2}\right)*d_{det}\right) \bigg/ d_{s2d}\right).$$

Figure 6:
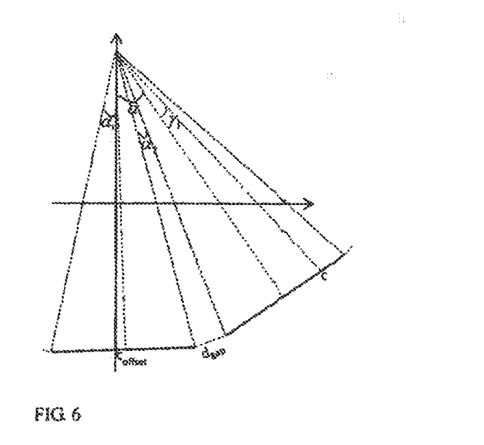
FIG. 6 shows the intermediate parameters used in fan-to-parallel data rebinning according to one embodiment of the invention.

FIG. 6 shows intermediate parameters used in fan-to-parallel data rebinning according to one embodiment of the invention, wherein α is the angle between central channels of two adjacent modules connecting with the x-ray source, $\alpha_1$ is the angle between the center and the edge of one module relative to the x-ray source, and $\alpha_2$ is the angle of the gap between two adjacent modules relative to the x-ray source, and $\gamma_1$ is the angle between the involved channel c and the central channel of the same module relative to the x-ray source. Moreover, $\gamma_{offset}$ is the offset angle between central channel of the detector array and the iso-ray, wherein the offset angle is introduced for double sampling and can be calculated as below:

$$\gamma_{offset} = \operatorname{atan}(c_{offset} * d_{det}/d_{s2d}).$$

After getting $\gamma_c$, the corresponding parallel view of angle θ is given by the following formula:

$$P(r,c,\theta) = F(r,c,\beta_v) = F(r,c,\theta-\gamma_c) \quad (4),$$

where 'P' is the output parallel-beam projection data, and 'F' is the input fan-beam projection data. Thus, the fan-to-parallel data re-sampling can be performed by formula (4) to thus obtain a corresponding relation between parallel beam projection data and fan beam projection data. For example, the projection data in parallel view of angle θ are rebinned from detector data having the angle $\theta_{-\gamma_c}$ in the fan beam projection data.

It should be understood that the above description is merely exemplary. In fact, the fan-to-parallel data rebinning can vary with geometric structure parameters of the flat module detector array. For example, parameters in the above formulas can be adjusted as necessary, for example, based on the number of modules, the number of packs in one module, the number of cells in one pack, and gaps, etc. For another example, when the gaps between modules and/or detector packs are very small, its effect on data rebinning can be ignored; or, when double sampling is unnecessary, the offset of the central channel relative to the iso-ray may not be taken into consideration.

According to one embodiment of the present invention, the fan-to-parallel data re-sampling utilizes the setting parameters of the CT scan. For example, the number of views in a single rotation of the detector around iso-center $v_{rot}$ can be utilized. To facilitate fan-to-parallel data conversion, replacing view angle with output view index v, we get the formula for fan-to-parallel data re-sampling:

$$P(r,c,v) = F(r,c,v-\gamma_c/\Delta\beta) \quad (5),$$

where P(r,c,v) refers to a parallel view with view index v and Δβ is the angle between two adjacent views ($\Delta\beta = 2\pi/v_{rot}$). As can be known from formula (5), the number of rows and channels is not changed by the re-sampling.

According to one embodiment of the invention, fan-to-parallel data re-sampling further comprises applying interpolation to the fan beam projection data. In this way, parallel beam projection data corresponding to $\gamma_c/\Delta\beta$ can be obtained. Particularly, when $\gamma_c/\Delta\beta$ is not an integer, the fan beam projection data should be interpolated to obtain the corresponding parallel beam projection data. Different interpolations are available, including but not limited to: Lagrange interpolation, linear interpolation, and polynomial interpolation.

According to one embodiment of the invention, the fan beam projection data is interpolated through a 6th order Lagrange interpolation. For example, if $\gamma_c/\Delta\beta = 100.25$, data of the 98th, 99th, 100th, 101st, 102nd, and 103rd views can be used to perform the Lagrange interpolation so as to obtain data of the desired view (i.e., view 100.25).

According to one embodiment of the invention, fan-to-parallel data rebinning further comprises equally spacing the parallel beam projection data with a predetermined space, wherein a corresponding relationship between the equis-paced parallel beam projection data and the parallel beam projection data prior to spacing can be obtained by equally spacing the parallel beam projection data. After converting fan beam data into parallel beam data, the obtained parallel beam data could be equally spaced to provide uniform detector spacing (parallel beam data spacing) with respect to the distance of the detector from the iso-center. A distance of a detector from the iso-center in parallel view is the distance of the detector in the fan view, which contributed to that detector in the parallel view, from the iso-center.

Figure 7:
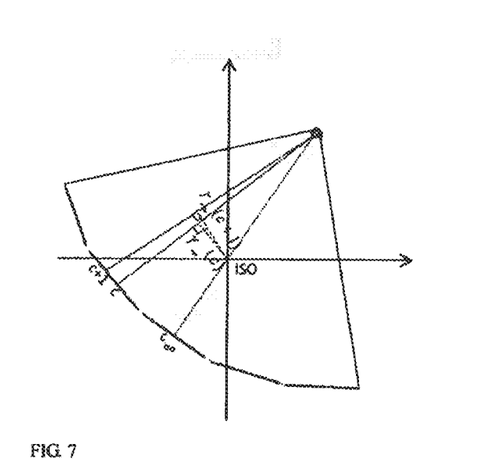
FIG. 7 shows the pre-determined distance used in equal spacing of parallel beam projection data according to one embodiment of the invention.

FIG. 7 shows the pre-determined distance used in equal spacing of parallel beam projection data according to one embodiment of the invention, wherein $\gamma_{mm}(c)$ is the distance of detector c from iso center; after re-spacing, $\gamma_{mm}(c+1) - \gamma_{mm}(c)$ should be equal for all pairs of adjacent detectors. We refer to this fixed increment as the distance between two adjacent samplings and denote it $\Delta\gamma_{mm}$.

According to one embodiment of the invention, the mapped distance of the distance between the iso channel and its adjacent channel at the iso center can be used as $\Delta\gamma_{mm}$ to equally space the parallel beam projection data. In this case, $\Delta\gamma_{mm}$ is defined as the length of an arc bounded by a single detector, wherein the arc is on a circle centered around the x-ray source with a radius $d_{s2i}$. The distance $\Delta\gamma_{mm}$ between two adjacent samplings in equally re-spaced parallel view could be calculated as:

$$\Delta\gamma_{mm} = d_{det}/d_{s2d} * d_{s2i} \quad (6).$$

Let c' be a detector channel index in the parallel view after the re-spacing, and c the corresponding detector channel in the parallel view before the re-spacing. The distance $\gamma_{mm}(c)$ of detector c' from the iso-center is calculated as:

$$\gamma_{mm}(c') = (c' - c_{ISO}) * \Delta\gamma_{mm} \quad (7).$$

Then, the distance of detector c' from iso-center imposes the angle at source $\gamma_c$ of the detector c:

$$\Delta_c = \operatorname{asin}(\gamma_{mm}(c')/d_{s2i}) \quad (8).$$

Finally, the formula for equal re-spacing could be obtained:

$$P_{eq}(r,c',v) = P(r,\gamma_c,v) \quad (9)$$

where $P_{eq}$ is the equally re-spaced parallel beam data, and P is the unequally spaced data after fan-to-parallel data re-sampling. Parallel beam projection data can be equally spaced through formula (9).

It should be understood that $\Delta\gamma_{mm}$ is here defined as the mapped distance of the distance between the iso channel and its adjacent channel at the iso center, but other spaces (e.g., larger or smaller than $\Delta\gamma_{mm} = d_{det}/d_{s2d} * d_{s2t}$) can also be used to equally re-space parallel beam projection data.

According to one embodiment of the invention, the re-sampled unequally spaced parallel beam projection data can be interpolated to obtain the required equally spaced parallel beam projection data based on the relationship between equally spaced parallel beam projection data and unequally spaced parallel beam projection data (i.e., the relation between channel index c' of equally spaced data and the angle $\gamma_c$ of data prior to equal spacing). For example, when $\gamma_c$ and the actual channel γ angle are not same, interpolation can be applied to obtain corresponding equally spaced parallel beam projection data. Different interpolations are available, including but not limited to: Lagrange interpolation, linear interpolation, and polynomial interpolation.

According to one embodiment of the invention, the unequally spaced parallel beam projection data can be interpolated through a 4th order Lagrange interpolation to obtain view data corresponding to $\gamma_c$.

It's worth noting that we should choose $\gamma$ angle for Lagrange interpolation to avoid the weighting error of cell length caused by the geometry of the flat detector array. However, if it is necessary, the detector channel index can also be used for interpolating unequally spaced parallel beam projection data.

According to one embodiment of the invention, if the CT system performs a helical scan, then the fan beam projection data obtained by the helical scan is firstly interpolated to obtain axial scan data and then fan-to-parallel data rebinning is performed to obtain parallel beam projection data.

According to one embodiment of the invention, the obtained parallel beam projection data can be used to generate a CT image, for example, based on a filtered back projection reconstruction algorithm or other algorithms. It should be understood that though a CT image with a better quality can be obtained by utilizing equally re-spaced parallel beam projection data, the CT image can also be generated by utilizing the parallel beam projection data prior to equal spacing when it is necessary.

Figure 8:
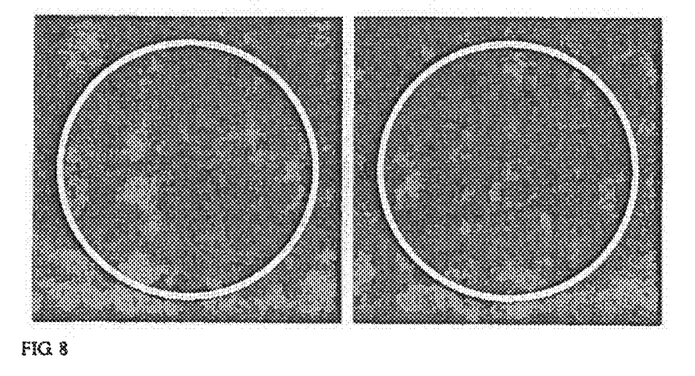
FIG. 8 shows a comparison between the CT image from one embodiment of the invention and the CT image from the prior art.

FIG. 8 shows a comparison between the CT image from the embodiments of the invention and the CT image from the prior art. For a flat module detector array, the imaging method of the prior art will cause severe ring artifacts (see the left figure), but the imaging method of the present invention will not lead to such ring artifacts (see the right figure).

According to one embodiment of the invention, the present invention is applicable not only to flat module detector arrays, but also to non-flat module detector arrays, such as curved detector arrays of the third generation CT systems. Persons skilled in the art could understand that by setting suitable geometric structure parameters (such as, the number of modules, the number of packs in one module, the gap between two adjacent modules and the gap between two adjacent packs) a flat module detector array actually is close to a curved detector array.

According to one embodiment of the invention, this embodiment can be applied to curved detector arrays (such as some CT products of GE) through the following settings: the number of detector modules in the flat module detector array is no less than 57; the number of the detector packs in each detector module is 1; the number of detector cells in each detector pack is no larger than 16; the gap between two adjacent modules is closer to 0; and the gap between two detector packs is close to 0.

Figure 9:
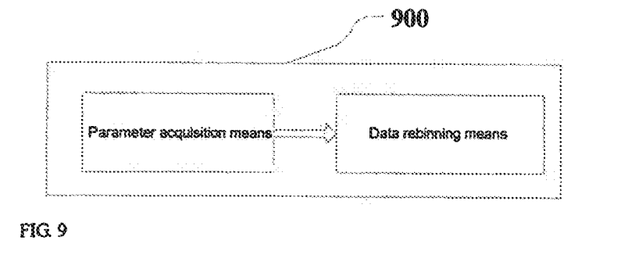
FIG. 9 shows an apparatus for imaging in the CT system according to one embodiment of the invention.

The present invention also provides an apparatus 900 for imaging in a CT system having flat module detector array, wherein the CT system obtains fan beam projection data of an object from a CT scan. The apparatus 900 as shown in FIG. 9 comprises: parameter acquisition means for acquiring a geometric structure parameter of the flat module detector array; and data rebinning means for rebinning data from fan beam data to parallel beam data based on the geometric structure parameter to convert the fan beam projection data into the parallel beam projection data. Then, the obtained parallel beam projection data is used by the CT system to generate a CT image.

According to the apparatus of one embodiment of the invention, data rebinning further comprises re-sampling data from fan beam data to parallel beam data based on the geometric structure parameter to obtain a corresponding relationship between the parallel beam projection data and the fan beam projection data.

According to the apparatus of one embodiment of the invention, re-sampling data further utilizes setting parameters of CT scan.

According to the apparatus of one embodiment of the invention, data re-sampling further comprises: applying interpolation to the fan beam projection data based on the corresponding relationship between the parallel beam projection data and the fan beam projection data.

According to the apparatus of one embodiment of the invention, rebinning data further comprises: equally spacing the parallel beam projection data to generate equispaced parallel beam projection data, wherein the corresponding relationship between the equispaced parallel beam projection data and the parallel beam projection data prior to spacing can be obtained by equally spacing the parallel beam projection data.

According to the apparatus of one embodiment of the invention, equally spacing the parallel beam projection data comprises: equally spacing the parallel beam projection data with a pre-determined distance.

According to the apparatus of one embodiment of the invention, equally spacing the parallel beam projection data comprises: applying interpolation to the parallel beam projection data based on the corresponding relationship between the equispaced parallel beam projection data and the parallel beam projection data prior to spacing.

According to the apparatus of one embodiment of the invention, the interpolation applied to the fan beam projection data is a 6th order Lagrange interpolation; and/or the interpolation applied to the parallel beam projection data is a 4th order Lagrange interpolation.

According to the apparatus of one embodiment of the invention, obtaining fan beam projection data of the object from the CT scan comprises: when the CT system performs a helical scan, interpolating the fan beam projection data obtained by the helical scan to obtain axial scan data.

According to the apparatus of one embodiment of the invention, the CT image is generated by utilizing the parallel beam projection data based on a filtered back projection reconstruction algorithm.

According to the apparatus of one embodiment of the invention, the apparatus is applicable to a curved detector array.

Meanwhile, an embodiment also provides a CT system comprising the method and/or apparatus for CT system imaging in accordance with any one of the above embodiments.

It is understandable to those skilled in the art that the present invention can be carried out through various familiar modes in the art, including but not limited to: hardware, firmware, computer program, and logic device, etc.

The embodiments of this invention have been illustrated in detail by means of foregoing descriptions and corresponding drawings. In addition, the specific terms used in the description are merely exemplary. Many modifications, equivalents, and variations of this invention will be apparent to those skilled in the art. For example, one step or module in the above embodiment may also be implemented through two or more steps or modules; or, two or more steps or modules or functions of the apparatus in the above embodiment can be realized in one step or module. As long as said variations are within the spirit and scope of the invention, they are regarded as falling within the protection scope of the present application, which is defined by the accompanying claims.

What is claimed is:

1. A method for imaging in a CT system having a flat module detector array, the method comprising:
obtaining fan beam projection data of an object from a CT scan;
obtaining a geometric structure parameter of the flat module detector array;
converting the fan beam projection data into parallel projection data, the conversion comprising:
rebinning data from the fan beam projection data based on the geometric structure parameter, wherein the rebinning comprises:
re-sampling the fan beam projection data based on the geometric structure parameter to obtain a relation between the fan beam projection data and corresponding parallel beam projection data, utilizing setting parameters of the CT scan; and
applying interpolation to the fan beam projection data based on the corresponding relation between the parallel beam projection data and the fan beam projection data, wherein the interpolation applied to the fan beam projection data is a 6th order Lagrange interpolation; and
generating a CT image from the parallel beam projection data.

2. The method in accordance with claim 1, wherein rebinning data further comprises equally spacing the parallel beam projection data to generate equispaced parallel beam projection data, wherein a corresponding relation between the equispaced parallel beam projection data and the parallel beam projection data prior to spacing can be obtained by equally spacing the parallel beam projection data.

3. The method in accordance with claim 2, wherein equally spacing the parallel beam projection data comprises equally spacing the parallel beam projection data with a pre-determined distance.

4. The method in accordance with claim 2, further comprising applying interpolation to the parallel beam projection data based on the corresponding relation between the equispaced parallel beam projection data and the parallel beam projection data prior to spacing.

5. The method in accordance with claim 1, wherein obtaining fan beam projection data of the object from the CT scan comprises: when the CT system performs a helical scan, interpolating the fan beam projection data obtained by the helical scan to obtain axial scan data.

6. The method in accordance with claim 1, wherein generating the CT image from the parallel beam projection data is based on a filtered back projection reconstruction algorithm.

7. The method in accordance with claim 1, wherein the method is applicable to a curved detector array.

8. An apparatus for imaging in a CT system having a flat module detector array and obtaining fan beam projection data of an object from a CT scan, the apparatus comprising:
a parameter acquisition device configured to acquire a geometric structure parameter of the flat module detector array; and
a data rebinning device configured to:
resample data from the fan beam projection data to the parallel beam projection data based on the geometric structure parameter to obtain a corresponding relation between the parallel beam projection data and the fan beam projection data, said resampling data based on setting parameters of the CT scan; and
apply an interpolation to the fan beam projection data based on the corresponding relation between the parallel beam projection data and the fan beam projection data, wherein the interpolation applied to the fan beam projection data is a 6th order Lagrange interpolation; and
an image generating device configured to generate a CT image utilizing the parallel beam projection data.

9. The apparatus in accordance with claim 8, wherein the data rebinning device is further configured to:
equally space the parallel beam projection data to generate equispaced parallel beam projection data, wherein a corresponding relation between the equispaced parallel beam projection data and the parallel beam projection data prior to spacing can be obtained by equally spacing the parallel beam projection data.

10. The apparatus in accordance with claim 9, wherein the data rebinning device is further configured to equally space the parallel beam projection data with a pre-determined distance.

11. The apparatus in accordance with claim 10, wherein the data rebinning device is further configured to:
apply interpolation to the parallel beam projection data based on the corresponding relation between the equispaced parallel beam projection data and the parallel beam projection data prior to spacing.

12. The apparatus in accordance with claim 11, wherein the interpolation applied to the parallel beam projection data is a 4th order Lagrange interpolation.

13. A CT system comprising:
an apparatus comprising:
a parameter acquisition device configured to acquire a geometric structure parameter of the flat module detector array; and
a data rebinning device configured to:
rebin data from fan beam data to parallel beam data based on the geometric structure parameter to convert the fan beam projection data into the parallel beam projection data, wherein each parallel beam projection data in a parallel view corresponds to the fan beam projection data having a same angle in the parallel view, said rebinning comprising:
resample data from the fan beam projection data to the parallel beam projection data based on the geometric structure parameter to obtain a corresponding relation between the parallel beam projection data and the fan beam projection data, said resampling data based on setting parameters of the CT scan; and
apply an interpolation to the fan beam projection data based on the corresponding relation between the parallel beam projection data and the fan beam projection data, wherein the interpolation applied to the fan beam projection data is a 6th order Lagrange interpolation; and
an image generating device configured to generate a CT image utilizing the parallel beam projection data.

* * * * *